Figure 1:
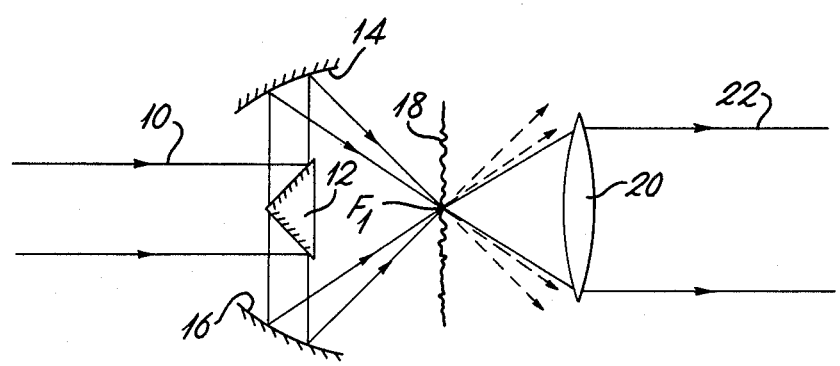

United States Patent [19]

Sinclair et al.

[11] 4,367,648
[45] Jan. 11, 1983

[54] DARK FIELD VIEWING APPARATUS

[75] Inventors: David A. Sinclair; Ian R. Smith, both of London, England

[73] Assignee: National Research Development Corporation, London, England

[21] Appl. No.: 245,547

[22] Filed: Mar. 19, 1981

[30] Foreign Application Priority Data

Mar. 25, 1980 [GB] United Kingdom ............... 8009980

[51] Int. Cl.³ ........................................... G01N 29/00
[52] U.S. Cl. ...................................... 73/620; 73/629
[58] Field of Search ............... 73/607, 606, 618, 620, 73/624, 627

[56] References Cited

U.S. PATENT DOCUMENTS 4,030,342 6/1977 Bond et al. .......................... 73/620
4,198,571 4/1980 Sheppard .......................... 250/571

FOREIGN PATENT DOCUMENTS 2821573 12/1978 Fed. Rep. of Germany ........ 73/606
1185919  3/1970 United Kingdom .
1509686  5/1978 United Kingdom .

*Primary Examiner*—Stephen A. Kreitman
*Attorney, Agent, or Firm*—Cushman, Darby & Cushman

[57] ABSTRACT

Dark field viewing apparatus comprises either (a) a source of coherent plane wave radiation and focused coherent receiving means, or (b) a source of focused coherent radiation and a coherent receiver of plane wave radiation, the source and receiver being axially aligned in both cases; and elimination means to eliminate any radiation which in the region of the focus would travel substantially parallel to the axis of the apparatus. The apparatus may be a transmission or a reflection scanning acoustic microscope or a holographic recording system, and the elimination means may be a small acoustically-absorbent stop.

32 Claims, 9 Drawing Figures

DARK FIELD VIEWING APPARATUS

A "dark field" mode is a mode in which radiation which is not deflected by an object is not detectable, while diffracted, refracted or scattered radiation can be sensed; both optical and scanning acoustic microscopes can be used in this mode. In conventional arrangements, both the illuminating system and the sensing system are focused onto the object and one of the systems is arranged off-axis so that directly transmitted radiation cannot be sensed. The disadvantages are that the focal regions of the systems must be very precisely alligned, and, with such asymmetric arrangements, most low spatial frequency radiation is lost, and only a fraction of high spatial frequency radiation is collected, so that the system is mainly sensitive to edges. The aim of the present invention is to overcome these disadvantages.

According to the invention, a method of examining an object in the dark-field mode comprises illuminating the object either with coherent plane wave radiation or with radiation convergent on a point in an object plane; receiving from the object by on-axis receiving means either coherent radiation divergent from a point in the object plane or plane wave coherent radiation respectively; and eliminating any radiation which in the region of convergence or divergence would travel substantially parallel to the direction of travel of the coherent plane wave radiation.

A preferred method comprises illuminating the object with coherent plane wave radiation; receiving radiation from the object by focused coherent radiation sensing means in axial alignment with the illuminating radiation; and eliminating any radiation which in the region of the focus would travel substantially parallel to the illuminating radiation.

Generally the method is applicable in the same circumstances as conventional dark field recording; i.e. when an object is highly transmissive so that either the deflection applied by the object to the illuminating beam affects only a very small proportion of the radiation, or the angle of deflection is very small. Elimination of radiation received parallel to the illuminating radiation allows the relatively small signal constituted by refracted, diffracted or scattered radiation to be sensed, and to achieve this a coherent spatially integrating sensing means is essential.

Also according to the invention, dark field viewing apparatus comprises a source either of coherent plane wave radiation or of radiation convergent on a point in an object plane; in axial alignment with the source receiving means for receiving either coherent radiation divergent from a point in an object plane or plane wave coherent radiation; and elimination means for eliminating any radiation which in the region of convergence or divergence would travel substantially parallel to the direction of travel of the coherent plane wave radiation.

In one arrangement the apparatus comprises a source of coherent plane wave radiation; a focused radiation receiver in axial alignment with the plane wave radiation, and elimination means for eliminating any radiation which in the region of the focus would travel substantially parallel to the plane wave radiation.

In one application of the invention, a dark field transmission scanning acoustic microscope comprises a first electroacoustic transducer arranged to provide plane wave acoustic radiation; in axial alignment with the transducer an electroacoustic lens having a second electroacoustic transducer and a curved surface to focus the second transducer on an axial point outside the lens; scanning means to cause relative movement in the focal plane between an abject and the focus of the electroacoustic lens; and elimination means to eliminate any radiation which in the region of the focal point would travel substantially parallel to said plane wave acoustic radiation. The elimination means may be an acoustically-absorbant stop on the axis between said axial focal point and the second transducer; or the second transducer may be an on-axis aperture. A dark field reflection scanning acoustic microscope may also be provided.

In both the transmission and the reflection microscope, there will also be provided exciting means to excite the first transducer or the transducer to provide plane wave illuminating radiation, and control, measuring, storage and display means to control the scan of the object, to measure and receive signals from the second or the transducer, to store the measured signals, and provide a two-dimensional display of the object.

In another application of the invention, a dark field holographic recording system comprises a laser; in axial alignment a beam splitter, first focusing means to focus the transmitted beam from the beam splitter, an opaque stop at the focus of the first focusing means, and second focusing means to focus plane wave radiation from the first focusing means onto an image plane; and plane reflecting means to reflect the reflected beam from the beam splitter onto the image plane.

The deviated beam acts as a holographic reference beam; if a photographic plate is placed in the image plane, presence of the reference beam renders it phase sensitive and only coherent light is recorded in a hologram.

Figure 2:
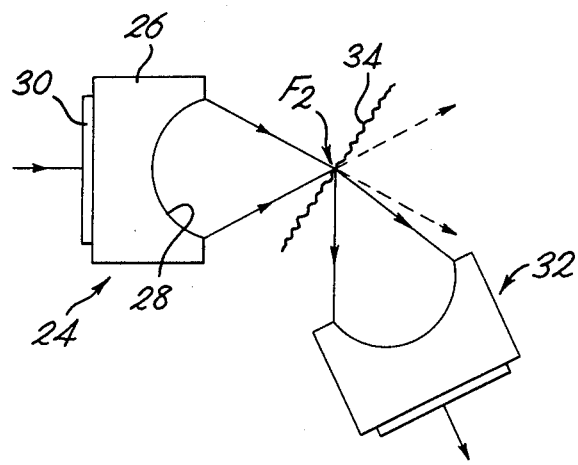
Figure 3:
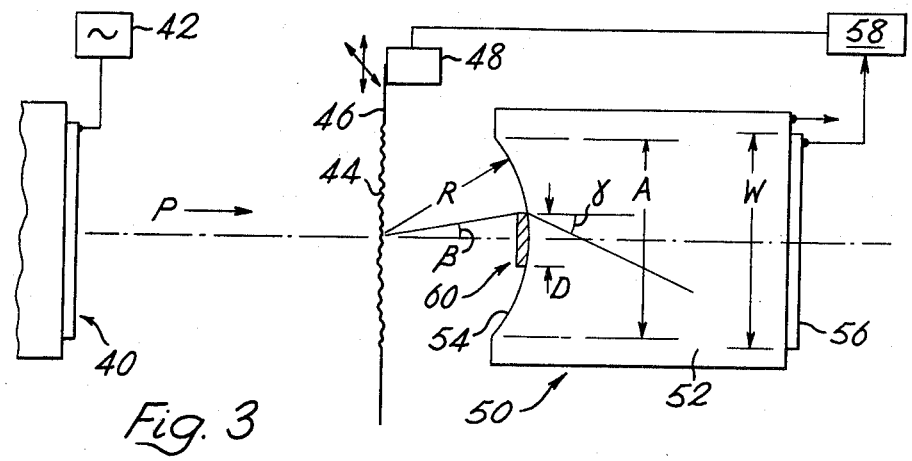
Figure 8:
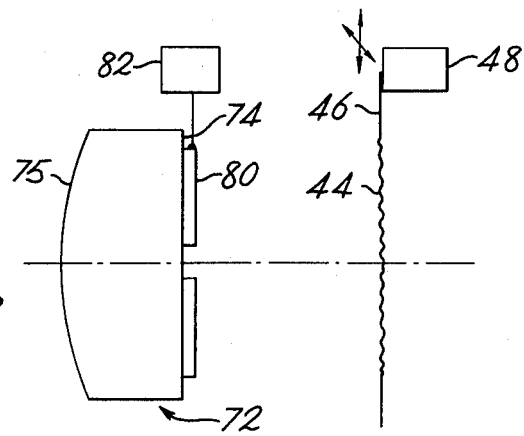

In the accompanying drawings,

FIGS. 1 and 2 illustrate respectively conventional optical and scanning acoustic microscopes arranged in the dark field mode. The invention will be described with reference to:

FIG. 3, which illustrates a transmission scanning acoustic microscope operating in the dark field mode;

FIGS. 4, 5, 6, and 7 which illustrate alternative transmission acoustic microscopes having different forms of receiving systems;

FIG. 8, which illustrates a reflection scanning acoustic microscope; and

Figure 9:
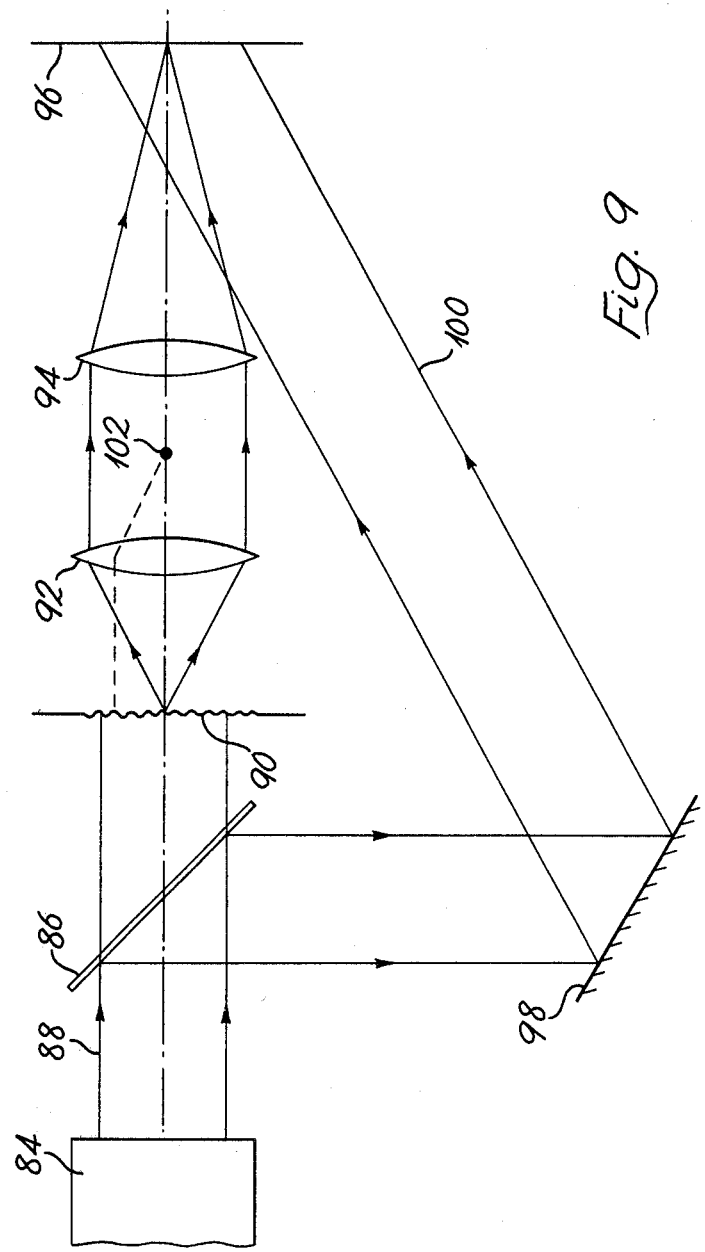

FIG. 9, which illustrates a dark field holographic recording system. In FIG. 1 a conventional optical dark field microscope comprises means for providing a plane wave illuminating beam 10 which is incident on two reflecting faces of a triangular prism 12 which divides the beam and reflects the halves through 90° to respective concave focusing mirrors 14, 16. The mirrors focus the beams to a point $F_1$ on the optical axis of the apparatus. This point defines a focal plane perpendicular to the incident beam at which an essentially transparent object 18 is placed. An objective lens 20, placed on-axis, is focused on point $F_1$ and provides an output beam 22.

Figure 6:
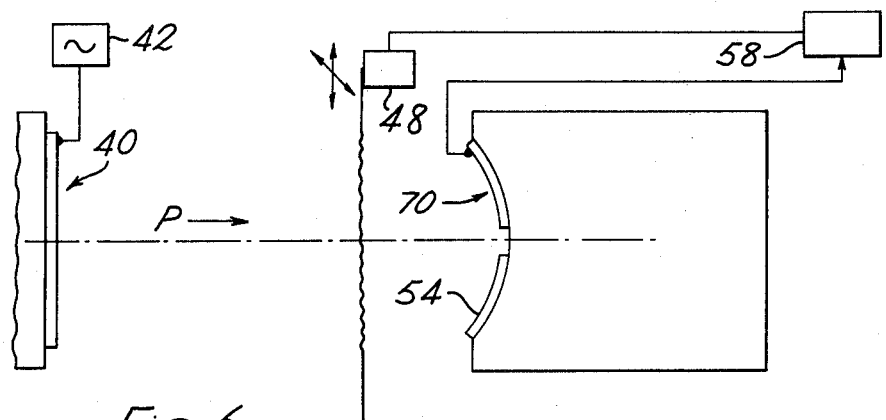

As can be seen from the diagram, light which passes undeviated through the object 18, as illustrated by the dotted lines, is not received by the lens 20, while light which is deviated is received. In this arrangement, the object is illuminated by off-axis beams and the objective lens 20 is on-axis. A similar arrangement is shown in FIG. 6 of U.S. Pat. No. 4,198,571 by C. J. R. Sheppard.

In FIG. 2 a dark field scanning acoustic microscope is illustrated which conforms to the requirements described in U.S. Pat. No. 4,030,342, by Bond, Cutler and Lemons, FIG. 8. An illuminating acoustic lens 24 consists of a solid body 26 having a curved face 28 at one end and a piezoelectric transducer 30 at the other. When the transducer is stimulated by a suitable input signal, an acoustic wave is produced which is focused by the curved face 28 to a focus $F_2$. A similar acoustic lens 32 forms the receiving lens and is also focused in point $F_2$. The lens 32 is arranged off-axis with respect to the transmitting lens so that undeviated radiation, as shown by the dotted lines, is not received. An object 34 is placed at the focus $F_2$ and in a plane which makes equal angles with the axes of both lenses. In use the object is scanned through the focus $F_2$ and the output signal from the acoustic lens 32 at each position in the scan contains information related to the acoustic transmission properties of the object 34.

The common features of the optical and acoustic microscopes shown in FIGS. 1 and 2 are that the object is arranged at the focus of both the illuminating and receiving systems, and one or other of the systems is off-axis.

In acoustic microscopes, the size of the focal spot may be very small, e.g. less than 1 micrometer in diameter, and alignment to this degree of precision is difficult.

In the arrangements according to the invention, there is only one focus, so this difficulty is not present.

In FIG. 3 a dark field scanning acoustic microscope according to the invention comprises a plane wave electroacoustic transducer 40 connected to an exciting source 42. Adjacent the transducer is a thin acoustically transmissive object 44 attached to a sample support 46 which is connected to scanning means 48. On the other side of the object is an electroacoustic lens 50 consisting of a lens rod 52 having a concave face 54 adjacent the object, and at the other end a receiving transducer 56 connected to an electrical control, measuring, storage and display circuit 58. At the centre of the curved face 54 is an acoustically absorbent stop 60.

In use the transducer 40 and curved face 54 are coupled to the object 44 by a water bath (not shown in FIG. 3) which may be a single drop of water. A plane acoustic wave generated by transducer 40 is incident on the object as indicated by the arrow P; the curvature of the face 54 is such that the part of the object on the axis of the apparatus is at the focus of the acoustic lens, and radiation passing through this part is converted by the receiving lens to an electrical signal which passes to the circuit 58. As in conventional acoustic microscopes the circuit controls the scanning means 48 to scan the object through the focus and to receive and store information at each point in the scan so that a two dimensional picture of the object is built up and displayed.

It is a property of the electroacoustic lens 50, as with most electroacoustic lenses, that it acts as a coherent detector i.e. it is phase sensitive; radiation incident in an essentially normal direction on the curved face 54 is sensed, while radiation incident at other angles is integrated over the surface to provide a relatively small sine wave component in the outer signal of the transducer 56. Since the object 44 is highly transmissive, most of the incident plane wave radiation will pass undeviated to the curved face 54. To provide a dark field mode, this radiation must be eliminated.

With a curved lens surface, the plane wave radiation is incident normal to the surface only very close to the optical axis. By placing a small stop 60 on the axis, directly-transmitted radiation is absorbed; plane wave radiation deviated by the object will be normally incident on other parts of the curved surface, and corresponding signals will be supplied to the circuit 58. Thus the microscope senses only radiation which has been deviated by the object, i.e. it operates in the dark field mode.

An alternative way of explaining the phenomenon is that the transducer 56 is sensitive to zero spatial frequency, i.e. plane wave radiation, but due to total internal reflection the active area of reception is confined to the central region of the lens. A diffracting object will produce higher order spatial frequencies to which the lens is sensitive but response th these frequencies is usually very small compared with the response to the zero order. By shielding the central region and eliminating the zero order, the higher frequencies, corresponding to the transmissive properties of the sample, can be detected.

The minimum width for the stop is determined by the degree of zero order suppression required. The zero order spatial frequency component incident on the lens produces a broad range of spatial frequencies within the lens rod. Since the receiving transducer has a finite width w, it will give an appreciable output for a range of incident spatial frequencies $\rho$ where:

$$|\rho| < 1/w \tag{1}$$

It is essential to make the stop diameter sufficiently large to block all of these components.

Using geometric optics it can be calculated that an acceptable minimum diameter D is given by $$D = \frac{4R\lambda}{(n-1)W} \tag{2}$$

where R is the radius of curvature of surface 54, $\lambda$ is the wavelength of the radiation in the lens rod 52 and n is the ratio between the acoustic velocity in the water and the acoustic velocity in the material of lens rod 52. However, it is necessary in a full analysis to take diffraction effects into account so that equation (2) becomes $$D = k \frac{4R\lambda}{(n-1)W} \tag{3}$$

where $k$ is dependent on the specific lens geometry used. Typical values for a system working at 10 MHz using a fused quartz lens material are $\lambda = 600$ $\mu$m, R = 16 mm, n = 4.3, W = 25 mm, $k = 5$ giving a value of D = 2.3 mm.

Referring agaain to FIG. 3, for the above typical values the stop intercepts all radiation diverging from the focus within a cone of half angle 1°, (angle $\beta$), and only radiation incident on the plane transducer at an angle of 4° or less will be sensed (angle $\gamma$).

It is essential to note that the operation of a microscope according to the invention depends on the use of a phase-sensitive receiving transducer. If an intensity-sensitive transducer were used, the stop would have to block all of the undeviated energy incident on the transducer and would have to be of much greater diameter, by at least a factor 2 for the values above.

The imaging equation of an acoustic microscope according to the invention can be derived from that of the conventional two-lens confocal scanning acoustic microscope. The transducer output voltage V(s) is given by:

$$V(S_x,S_y) = \int\int t(x-S_x, y-S_y)U_1(x,y)dxdy \quad (4)$$

where, in cylindrical co-ordinates, x, y are the scan plane co-ordinates, $S_x$, $S_y$ are the object scan co-ordinates, $U_1(x, y)$ is the lens sensitivity function and $t(x, y)$ is the transmittance of the object. Thus the lens sensitivity is convolved with the transmittance of the object. An approximate expression for the lens sensitivity function can be written in radial co-ordinates as:

$$U_1(r) \alpha \frac{A \cdot J_o(\pi Ar/\lambda F)}{\pi Ar/\lambda F} - \frac{D \cdot J_o(\pi Dr/\lambda F)}{\pi Dr/\lambda F} \quad (5)$$

when $J_o$ is the Bessel function of the first order, F is the focal length of the lens, A is lens aperture, D the stop diameter and $\lambda$ the wavelength and r is the radial co-ordinate. The effect of the aperture stop is to narrow the central lobe of the lens sensitivity and to increase the side lobe level.

In addition to the advantage that a precisely confocal system is no longer required, other advantages are that the system is circularly symmetrical; the spatial frequency response of the system is symmetrical; and, for a given aperture, the lens collects as much as possible of the diffracted energy up to its normal acceptance limit. Although the system suffers a slight loss in resolution over a confocal arrangement because there is only one lens, it is still diffraction limited.

Other embodiments according to the invention will now be described.

Figure 4:
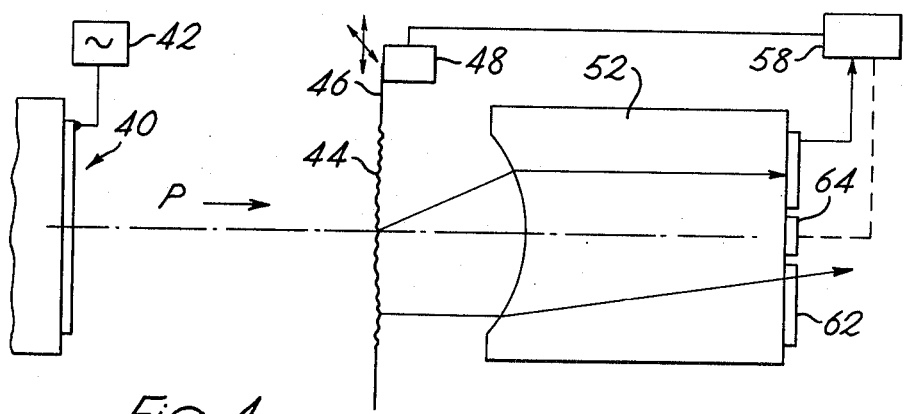

FIG. 4 is very similar to FIG. 3 and identical items are given the same reference numerals. The difference is that the stop 60 is absent, and the receiving transducer is in the form of a large outer annulus 62 surrounding a small central circular part 64, each connected to the control circuit 58. The central part 64 is equivalent to the stop 60 in FIG. 3 and when this part of the transducer is disconnected by a switch within circuit 58, the FIG. 4 arrangement comprises a dark field microscope. When the central part 64 is switched into the circuit, the arrangement can be used as a conventional bright-field scanning acoustic microscope.

Figure 5:
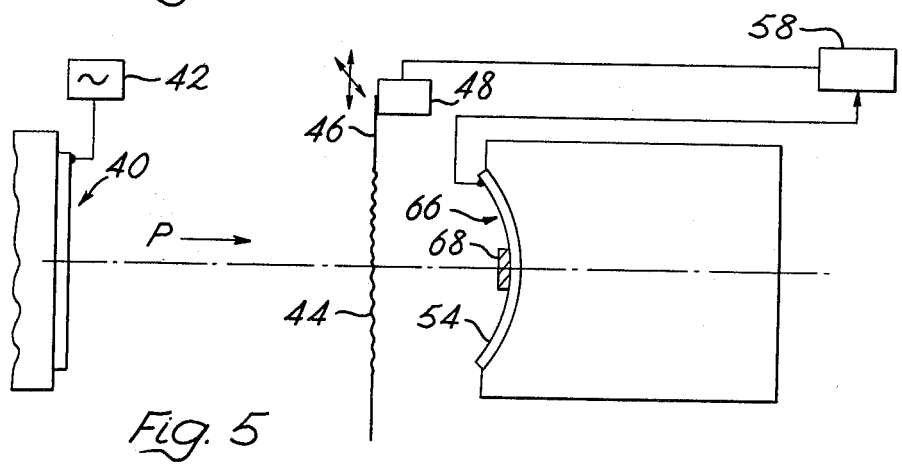

In FIGS. 5 and 6, the plane receiving transducer 56 of FIG. 3 is omitted, and the curved surface 54 carries a curved piezoelectric transducer. In FIG. 5 the curved transducer 66 covers the whole of the surface 54, and an acoustically absorbing stop 68 is placed on the optical axis to absorb the undeflected plane wave radiation. In FIG. 6 the curved transducer is annular in shape with a central aperture so that the undeflected plane wave radiation is not received.

Figure 7:
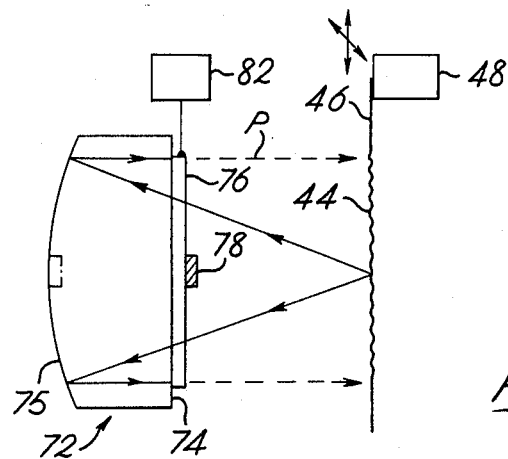

It is also known that acoustic microscopes can operate in a reflective mode. Such a microscope can be modified to give a dark-field image, as shown in FIGS. 7 and 8. An acoustic transmitter/receiver 72 consists of a body of material having a flat face 74 which carries a flat piezoelectric transducer, this face being adjacent the object 44. The opposite end 75 of the body is curved and can reflect acoustic radiation. In FIG. 7 the transducer 76 covers the whole of the flat face and is provided with a central acoustically absorbent stop 78, and in FIG. 8 the transducer 80 is annular in form with a central aperture. In both cases the transducer is connected to a control and measuring circuit 82 which also provides an exciting signal to the transducers so that a plane acoustic wave is generated and, as shown by the broken lines, illuminates the object. Radiation reflected by the object at the focus of the curved surface 75 is reflected by that surface back towards the plane transducer as a plane wave, which is sensed by the transducer. Plane wave radiation reflected by the object 44 along the optical axis is not received, because of the presence of the stop 78 of the annular form of transducer 80, and a dark field mode of operation is achieved. As is usual with reflective mode microscopes, a pulse gating technique must be applied to allow reflected signals to be sensed.

In any of the illustrated embodiments in which a transducer having a central aperture is provided, an independently switchable central part may be provided to allow use in the bright field mode.

As is frequently the case with scanning acoustic microscopes, the transmitting and receiving transducers are interchangeable in many arrangements according to the invention. Thus in FIGS. 3 to 8, the object can be illuminated with convergent radiation, rays close to the optical axis being eliminated by a stop, and collimated radiation is detected.

All of the illustrated embodiments described above are acoustic in nature; all electroacoustic transducers have the property required in accordance with the present invention, i.e. they are always phase sensitive. The invention can also be applied optically if a phase sensitive optical sensor can be provided, but most optical sensors are not sensitive to phase. Usually the sensor will also need to be spatially integrating as in the acoustic embodiments, but an optical example in which spatial coherence is not a requirement is illustrated in FIG. 9 which shows a holographic system. It is believed that this is the first time that holography has been applied in a dark-field mode.

In FIG. 9, a laser 48 illuminates a beam splitter 86 with a coherent beam of plane wave light 88. The directly transmitted part of the split beam illuminates an object 90, and light transmitted by the object passes through a first convex lens 92, which is focused on the object, and through a second convex lens 94 to a photographic plate 96 in the image plane of the second lens. The deviated part of the split beam is reflected by a plane mirror 98 onto the plate 96 and acts as a holographic reference beam 100.

Since the object 90 is in the focal plane of the first lens 92, light diffracted by the object passes from lens 92 to lens 94 in plane wave form as shown by the full lines. Conversely, plane wave radiation entering lens 92 is focused by the lens to a position between lenses 92 and 94, as shown by the broken line. An opaque stop 102 is placed on the optical axis at this position, and therefore shields the photographic plate from radiation passing undeviated through the sample. The use of the reference beam 100 renders the photographic plate 96 phase sensitive, and a hologram of the dark-field transmission properties of the object is recorded.

It should be noted that the arrangement provides a conventional imaging system, and it is not necessary to provide a scanning system. It is a great advantage that, by selection of a beam splitter 86 having the appropriate property, the intensities of the reference beam and the information-carrying beam from the sample as it reaches the photographic plate can be equalised to give ideal holographic recording conditions. By varying the magnification of the lenses 92, 94, conventional optical magnification can be provided.

We claim:

1. Dark field viewing apparatus comprising:
a source of acoustic radiation;
spatially integrating acoustic receiving means disposed in axial alignment with the source; and
on-axis elimination means;
one of the source and the receiving means being focused on a point in an object plane, and the elimination means eliminating any acoustic radiation which in the region of the focus in the object plane would travel substantially parallel to the axis of the apparatus.

2. Dark field viewing apparatus according to claim 1 in which:
said source is a source of coherent plane wave acoustic radiation;
said receiving means is a spatially integrating acoustic receiving means for receiving and spatially integrating coherent acoustic radiation divergent from a point in said object plane;
said elimination means is for eliminating any acoustic radiation which in the region of divergence would travel substantially parallel to the direction of travel of the coherent plane wave acoustic radiation.

3. Apparatus according to claim 2
in which said receiving means is a focused spatially integrating acoustic radiation receiver in axial alignment with the plane wave radiation; and
in which said elimination means eliminates any acoustic radiation which in the region of said focus would travel substantially parallel to the plane wave radiation.

4. Apparatus according to claim 3 wherein:
said acoustic radiation source includes a first electroacoustic transducer arranged to provide plane wave acoustic radiation;
said receiving means including an electroacoustic lens in axial alignment with said transducer and having a second, spatially integrating, electroacoustic transducer and a curved surface for focusing the second transducer on an axial point outside the lens;
there being scanning means to cause relative movement in the focal plane between an object and the focus of said electroacoustic lens; and
said elimination means operating to eliminate any acoustic radiation which in the region of the focal point would travel substantially parallel to said plane wave acoustic radiation.

5. Apparatus according to claim 4 in which the elimination means is an acoustically-absorbent stop on the axis between said focal point and the second transducer.

6. Apparatus according to claim 4 in which the second transducer has an on-axis aperture.

7. Apparatus according to claim 4 in which said second transducer conforms to said curved focusing surface.

8. Apparatus according to claim 7 in which the elimination means is an acoustically-absorbent stop on the axis between said axial focal point and the second curved transducer.

9. Apparatus according to claim 7 in which the second curved transducer has an on-axis aperture.

10. Apparatus according to claim 4, further comprising:
exciting means to excite the first transducer;
control means to control the scanning means;
measuring means to measure signals received from the second transducer;
storage means to store the measured signals; and
display means to provide a display of an image formed from the stored signal.

11. Apparatus according to claim 3 wherein:
said receiver includes an electroacoustic lens having a plane surface at one end, a convex focusing surface at the other end, and a plane spatially integrating electroacoustic transducer in contact with the plane surface;
there being scanning means to cause relative movement in the focal plane of the lens between an object and the focus of the lens, and
said elimination means operating to eliminate any acoustic radiation which in the region of the focus would travel substantially parallel to the axis of the lens.

12. Apparatus according to claim 11 in which the elimination means comprises an acoustically absorbent stop on the axis between the object and the plane transducer.

13. Apparatus according to claim 11 in which the plane transducer has an on-axis aperture.

14. Apparatus according to claim 11 further comprising:
control means to control the scanning means;
measuring means to measure signals received from the second transducer;
storage means to store the measured signals; and
display means to provide a display of an image formed from the stored signal.

15. Dark field viewing apparatus according to claim 1 in which:
said source is a source of acoustic radiation convergent on a point in an object plane;
said receiving means is a spatially integrating acoustic receiving means disposed in axial alignment with the source for receiving plane wave coherent acoustic radiation and for spatially integrating the received radiation; and
said elimination means eliminates any acoustic radiation which in the region of convergence would travel substantially parallel to the direction of the coherent plane wave acoustic radiation.

16. Apparatus according to claim 15:
in which said source is focused on a point in the object plane, and
in which said elimination means eliminates any acoustic radiation which in the region of said focus would travel substantially parallel to the plane wave radiation.

17. Apparatus according to claim 16 including:
an electroacoustic lens having a first electroacoustic transducer and a curved surface for focusing said transducer on an axial point outside the lens;
in axial alignment with the electroacoustic lens a second, spatially integrating, electroacoustic transducer;
scanning means to cause relative movement in the focal plane between an object and the focus of the electroacoustic lens; and
elimination means to eliminate any acoustic radiation which in the region of the focal point would travel substantially parallel to said plane wave acoustic radiation.

18. Apparatus according to claim 17 in which the elimination means is an acoustically-absorbent stop on the axis between said axial focal point and the second transducer.

19. Apparatus according to claim 17 in which the second transducer has an on-axis aperture.

20. Apparatus according to claim 17 in which said second transducer conforms to said curved focusing surface.

21. Apparatus according to claim 20 in which the elimination means is an acoustically-absorbent stop on the axis between said focal point and the second curved transducer.

22. Apparatus according to claim 20 in which the second curved transducer has an on-axis aperture.

23. Apparatus according to claim 17, further comprising:
   exciting means to excite the first transducer;
   control means to control the scanning means;
   measuring means to measure signals received from the second transducer;
   storage means to store the measured signals; and
   display means to provide a display of an image formed from the stored signal.

24. Apparatus according to claim 16 including:
   an electroacoustic lens having a plane surface at one end, a convex surface at the other end, and a plane spatially integrating electroacoustic transducer in contact with the plane surface;
   scanning means to cause relative movement in the focal plane of the lens between an object and the focus of the lens; and
   elimination means to eliminate any acoustic radiation which in the region of the focus would travel substantially parallel to the axis of the lens.

25. Apparatus according to claim 24 in which the elimination means comprises an acoustically-absorbent stop on the axis between the object and the plane transducer.

26. Apparatus according to claim 24 in which the plane transducer has an on-axis aperture.

27. Apparatus according to claim 24 further comprising:
   control means to control the scanning means;
   measuring means to measure signals received from the second transducer;
   storage means to store the measured signals; and
   display means to provide a display of an image formed from the stored signal.

28. A method of examining an object in the dark-field mode comprising the steps of:
   illuminating the object with acoustic radiation;
   on-axis spatially integrating acoustic radiation received from said object, and
   axially eliminating part of the acoustic radiation;
   one of the said illuminating and integrating steps being practiced with radiation passing substantially through a point in the plane of the object, and the axially eliminating step being practiced on radiation which in the region of said point would travel substantially parallel to the general direction of travel of the acoustic radiation.

29. A method according to claim 28 wherein:
   said object is illuminated with coherent plane wave acoustic radiation;
   said integrating step includes on-axis spatially integrating coherent acoustic radiation received from said object and divergent from a point in an object plane; and
   said eliminating step includes eliminating any radiation which in the region of divergence would travel substantially parallel to the direction of travel of the coherent plane wave radiation.

30. A method according to claim 29 in which:
   radiation from the object is received and spatially integrated by focusing coherent acoustic radiation sensing means in axial alignment with the illuminating radiation; and
   said eliminating step includes eliminating any radiation which in the region of the focus would travel substantially parallel to the illuminating radiation.

31. A method according to claim 28 wherein:
   said object is illuminated with acoustic radiation convergent on a point in an object plane;
   said integrating step includes on-axis spatially integrating plane wave coherent acoustic radiation received from said object; and
   said eliminating step includes eliminating any radiation which in the region of convergence would travel substantially parallel to the direction of travel of the coherent plane wave radiation.

32. A method according to claim 31 in which:
   the object is illuminated by a focused acoustic radiation source focused on a point in the object plane; and
   said eliminating step includes eliminating any radiation which in the region of the focus would travel substantially parallel to the direction of travel of the coherent plane wave radiation.

* * * * *